(12) United States Patent
Evans et al.

(10) Patent No.: US 6,916,914 B1
(45) Date of Patent: Jul. 12, 2005

(54) PURIFICATION OF SOMATOTROPIN FROM TRANSFORMED MICROORGANISMS

(75) Inventors: Timothy W. Evans, Three Rivers, MI (US); Mark W. Knuth, Madison, WI (US)

(73) Assignee: Pharmacia & Upjohn Co., Kalamazoo, MI (US)

( * ) Notice: Subject to any disclaimer, the term of this patent is extended or adjusted under 35 U.S.C. 154(b) by 0 days.

(21) Appl. No.: 08/256,297

(22) PCT Filed: Jun. 13, 1986

(86) PCT No.: PCT/US86/01289

§ 371 (c)(1),
(2), (4) Date: Feb. 3, 1987

(87) PCT Pub. No.: WO87/00204

PCT Pub. Date: Jan. 15, 1987

Related U.S. Application Data

(63) Continuation of application No. 06/749,016, filed on Jun. 26, 1985, now abandoned.

(51) Int. Cl.$^7$ .............................. A23J 1/00; C07K 14/00
(52) U.S. Cl. ....................... 530/422; 530/350; 530/351; 530/399; 435/69.4
(58) Field of Search ........................... 514/12; 530/412, 530/399, 350, 351, 422; 435/69.1, 69.4

(56) References Cited

U.S. PATENT DOCUMENTS

| | | | | |
|---|---|---|---|---|
| 4,443,539 A | * | 4/1984 | Fraser et al. | 435/69.4 |
| 4,511,502 A | * | 4/1985 | Builder et al. | 530/417 |
| 4,511,503 A | * | 4/1985 | Olson et al. | 530/422 |
| 4,512,922 A | * | 4/1985 | Jones et al. | 530/408 |
| 4,518,526 A | * | 5/1985 | Olson | 530/351 |
| 4,599,197 A | * | 7/1986 | Wetzel | 530/405 |
| 4,612,367 A | * | 9/1986 | Grinnan et al. | 530/399 |
| 4,620,948 A | * | 11/1986 | Builder et al. | 530/419 |
| 4,652,630 A | * | 3/1987 | Bentle et al. | 530/344 |

FOREIGN PATENT DOCUMENTS

| | | | |
|---|---|---|---|
| EP | 47 600 | | 8/1981 |
| EP | 103 395 | | 8/1983 |
| EP | 114 506 | | 12/1983 |
| EP | 131 843 A1 | | 7/1984 |
| GB | 2073245 | | 3/1981 |
| GB | 2073245 | * | 10/1981 |

OTHER PUBLICATIONS

Wetzel etal. Biochemistry 19 6096–6104 1980.*
D.V. Goeddel et al., Direct Expression in *Escherichia coli* of a DNA Sequence Coding for Human Growth Hormone, Nature 281:544–548 (1979).
A.C. Paladini et al., Molecular Biology of Growth Hormone, CRC Reviews in Biochem., 15(1):25–56 (1983).
P.J. Eppard and D.E. Bauman, The Effect of Long–Term Administration of Growth Hormone on Performance of Lactating Dairy Cows, Proc. 1984 Cornell Nutrition Conf. for Feed Manufacturuers, pp. 5–17.
B.E. Schoner et al., Role of mRNA translational efficiency in bovine growth hormone expression in *Escherichia coli*, PNAS, USA, 81:5403–5407 (1984).
P.H. Seeburg et al., Efficient Bacterial Expression of Bovine and Porcine Growth Hormones, DNA, 2(1):37–45 (1983).
G. Gray et al., Synthesis of bovine growth hormone by Streptomyces lividans, Gene 32:21–30 (1984).
R.G. Schoner et al., Isolation and Purification of Protein Granules from *Escherichia coli* Cells Overproducing Bovine Growth Hormone, Bio/Tech., 3:151–154 (1985).
M. Teuber, Archiv fur Mikrobiologie 55:31–45 (1966); Chem. Abstracts, Abstract 16597y, 66(5): 1593–1954, Jan. 30, 1967.
A.M. Plommet et al., Ann. Rech. veter., 5(2):213–221 (1974); Chem. Abstracts, Abstract 100544w, 81(17):138, Oct. 28, 1974.
B.D. Davis et al., Inactivation of Viruses, Microbiology, 3rd edition, Harper & Row, New York (US), pp. 1271–1274 (1980).

* cited by examiner

Primary Examiner—Remy Yucel
(74) Attorney, Agent, or Firm—James D. Darnley, Jr.

(57) ABSTRACT

This invention discloses a commercially advantageous process for extraction and purification of protein from microorganisms. The initial steps of the process are useful for purifying many insoluble proteins while later steps are designed to renature denatured somatotropins produced by transformed microorganisms. The process is especially useful for purifying recombinantly-produced bovine somatotropin.

12 Claims, No Drawings

PURIFICATION OF SOMATOTROPIN FROM TRANSFORMED MICROORGANISMS

This application is a continuation-in-part of U.S. Ser. No. 06/749,016, filed Jun. 26, 1985, now abandoned.

BACKGROUND OF THE INVENTION

FIELD OF THE INVENTION

This invention discloses a commercially advantageous process for extraction and purification of protein from microorganisms. The initial steps of the process are useful for purifying many insoluble proteins while later steps are designed to renature denatured somatotropins produced by transformed microorganisms. The process is especially useful for purifying recombinantly-produced bovine somatotropin (rbSt).

Somatotropins are growth hormones which were originally discovered in pituitary gland extracts of various animals. In general, somatotropins are conserved molecules and similarities in amino acid sequence and structure are found between animals of disparate evolutionary ranking evidencing a common ancestral relationship.

Somatotropins are globular proteins comprised of a single chain of approximately 200 amino acids, having 2–3 intrachain disulfide bonds. Accordingly, bovine somatotropin (bSt) is comprised of a single chain of 190–191 amino acids, a globular structure with two intrachain disulfides, and a molecular weight of approximately 22,000 daltons.

BSt is able to remain insoluble in an aqueous environment when in the reduced state. This characteristic is exploited in the present invention as it relates to extraction and purification procedures. The disclosed process is applicable for other somatotropins having this same characteristic.

Growth hormones especially bSt have great commercial potential. Growth hormones in general have been shown to increase the growth rate of cattle, hogs and salmon, along with a significant increase in the meat to fat ratios. Moreover, bSt has value in its proven ability to increase milk production in dairy cattle. It is presently anticipated that 5–50 mg of growth hormone will be necessary per day per animal to achieve effective results.

Although a number of processes are presently available for the extraction of somatotropins from *E. coli* or other microorganisms on a laboratory scale, a process for the commercial production or large scale production of bioactive somatotropins, especially bST, was not available up until now. The disclosed process optimizes recovery of somatotropins from a microorganism when that microorganism has produced the somatotropin in predominantly precipitated form rather than as a soluble protein. These precipitated somatotropins are often deposited in refractile bodies within the microorganism. The refractile bodies are visible under a light microscope.

Somatotropins are not the only heterologous proteins to form retractile bodies inside microorganisms. Refractile bodies are often produced as a result of overproduction of a protein. They are thought to be an internal storage mechanism. Refractile bodies are commonly seen in microorganisms expressing heterologous proteins due to pathogenic conditions, mutations or recombinant genetic transformation.

Precipitated somatotropins are thought to be in a reduced state when found in refractile bodies of transformed microorganisms such as *E. coli*. Although expression of eukaryotic protein in *E. coli* or other prokaryote systems can yield a amino acid chain identical to the natural product often times the secondary and tertiary structure of the native protein cannot be forced or duplicated by the prokaryote. Unless the energy state of the native form forces the product to the native conformation, chemical and thermal intervention will be necessary to yield a biologically active and non-antigenic product.

BSt has 4 cysteine residues for which 3 different arrangements of disulfide bonds are possible in the oxidized monomeric state, only one of which is native. Upon workup without the precautions disclosed herein the cysteine residues will oxidize using available oxygen to form both polymeric and monomeric bSt with random disulfides. The random states so generated result in substantial yield reductions of bioactive growth hormones.

The classical studies of protein folding involving reduction and reoxidation of proteins were performed on enzymes such as ribonuclease (RNAse) and lysozyme. Givol, D., DeLorenzo, F., Goldberger, R. F., and Anfinsen, C. B., Biochemistry 53:676–684 (1965); and Saxena, V. P., and Wetlaufer, D. B., Biochemistry 9(25):5015–5022 (1970). The proteins are typically reduced with B-mercaptoethanol (BME) or dithiothreitol (DTT) in the presence of a denaturant such as 6–8 M urea or guanidine-HCl. The reductant and denaturant is then removed by gel filtration, and the protein is allowed to air-oxidize at low concentration.

The mechanism presently accepted for the reoxidation of reduced proteins involves rapid reoxidation of the protein to form random disulfide bonds, followed by disulfide interchange ("shuffling"). Although the protein may form incorrect disulfide bonds at first, these disulfides may be reduced again by reaction with free thiol groups on other proteins or thiol reagents. This gives each protein molecule the chance to assume a variety of disulfide bonding modes until the majority of the molecules are in the lowest energy configuration. The lowest energy state is usually the native conformation. Acharya, A. S., and Taniuchi, H., Molec. and Cell. Biochem. 44:129–148 (1982); and Anfinsen, C. B., Science 181:223–230 (1973).

Unlike the proteins described above, fully reduced bSt is insoluble in most aqueous solvents. Thus, many of the classical techniques for oxidation of reduced proteins are not applicable to bSt and the available methods taught in the literature concerning rbSt purification from *E. coli* were not practical for commercial applications.

The available literature discloses general principles of purification of heterologous proteins from microorganisms. Basically the steps involve cell kill, lysis, selective solubilizing of host debris, mechanical collection of the precipitated heterologous protein and solubilizing the heterologous protein followed by further filtration steps.

Prior to this invention, it was not possible to kill host cells without a concomitant precipitation of large amounts of undesired protein and other host cell debris. The precipitation of undesired protein along with desired insoluble proteins adds to the complexity of downstream purification procedures. This invention discloses the use of nonpolar organic solvents to kill cells. By eliminating standard killing steps using heat, phenol or combinations of phenol and toluene and by using the nonpolar organic solvents disclosed herein, it is possible to minimize unwanted host protein precipitation.

This invention also provides for an effective one step renaturation of somatotropins in the presence of detergents. Prior art recommendations suggest that renaturing of any desired protein to its native state had to be done at low concentrations of less than 1 mg/ml to avoid polymerization of bSt through cysteine residues. This invention resolves that problem by avoiding solubilization of somatotropins in nondetergent chaotropic agents such as urea or guanidine. By using mild detergents to solubilize the somatotropins, this invention demonstrates that it is possible to renature rbSt and like somatotropins at concentrations greater than 15 mg/ml.

The disclosed process has other advantages over the prior art processes. This process eliminates the need for thiol-reducing agents such as mercaptoethanol or glutathione. There is no need to use high concentrations of denaturants such as urea or guanidine to solubilize the desired proteins. Urea and guanidine have to be used at molar concentrations of up to 9 moles per liter and such concentrations will inevitably cause problems in large scale purifications resulting in increased production costs. This procedure also provides for alternatives to sodium dodecyl sulfate (SDS) as a solubilizing detergent which are advantageous because SDS is known to be difficult to remove from bSt. Dellacha, J. M., Annals N.Y. Acad. Sci., 148:313–327 (1968). One further advantage of this procedure is that bSt is split into two discrete populations upon removal of detergent. Upon removal of detergent, rbst is found as either a soluble monomer or as an insoluble aggregate which is readily removable. The proportion of dimers or trimers is not significant and their removal by gel filtration or by ion exchange chromatography is optional.

Lastly, the disclosed process is more economical when compared to alternative purification procedures.

Using the disclosed procedure, yields of up to 60% of the rbSt produced by the organism can be obtained. The rbSt is in the native and bioactive form as determined by in vivo tests in hypophysectomized rats. Parlow, A. F., et al., Endocrin. 77:1126 (1965).

Information Disclosure

Expression of somatotropins from a variety of animals by transformed microorganisms is known. Goeddel, D. V. et al, "Direct Expression in *Escherichia coli* of a DNA sequence coding for human growth hormone", Nature 281, 544–548 (1979) and Seeburg, P. H. et al, "Efficient Bacterial Expression of Bovine and Porcine Growth Hormones", DNA 2:37–45 (1983).

Naturally occuring bSt is a mixture of heterogeneous proteins, the amino acid sequences of which are known. Paladini, A. C., et al., Molecular Biology of Growth Hormone, CRC Reviews in Biochem., 15(1):25–56 (1983). The naturally occurring mixtures have been purified from pituitary glands of cattle. The commercial potential is well recognized and documented by biological studies on both dairy and feed cattle. Eppard, P. J. and Bauman, D. E., The Effect of Long-Term Administration of Growth Hormone on Performance of Lactating Dairy Cows; and Bauman,. D. E., Effect of Growth Hormone on Growth Rates and Mammary Development of Ruminants, Proc. 1984 Cornell Nutrition Conference for Feed Manufacturers, pp. 5–17, published by Cornell University, Ithaca, N.Y.

The production of bSt in transformed microorganisms can be achieved by a variety of recombinant genetic plasmids. University of California, DNA Transfer Vectors Coding for Bovine Growth Hormone, . . . , and Useful for Transforming Microorganisms for Production of Fusion Proteins, European Patent Application 47 600; Yeda Research and Development Company, Production of Bovine Growth Hormone by Microorganisms; United Kingdom Patent Application; GB 2073245A; and Schoner, B. E. et al., Role of mRNA Translational Efficiency in Bovine Growth Hormone Expression in *Escherichia coli,* PNAS USA, 81:5403–5407 (1984).

Analogs of bSt are also known. Biogen NV, DNA Sequences, Recombinant DNA Molecules and Processes for Producing Bovine Growth Hormone-Like Polypeptides in High Yield, European Patent Application 103 395; and Schoner, B. E., et al., Supra. Unlike the present invention these analogs of bSt relate to the insertion of bases at the 5' and 3' ends of bSt creating a protein different from the naturally-occurring amino acid sequences.

The production of bSt in transformed microorganisms other than *E. coli* has been reported. Gray, G., et al., Synthesis of Bovine Growth Hormone by Streptomyces lividans, Gene, 32:21–30 (1984); and in Yeast, U.S. Pat. No. 4,443,539.

The methods of culturing and fermenting the transformed microorganisms is also known and fully described in the above-cited literature.

Purification of biologically active bSt from transformed cells has also been described previously. Genentech, Inc., "Purification and Activity Assurance of Precipitated Heterologous Proteins", U.S. Pat. Nos. 4,511,502; 4,511,503; 4,512,922 and 4,518,526; Biotechnology General Corp., "Expression Vectors for Enhanced Production of Polypeptides . . . and Related Methods", European Patent Application 131 843; and, Schoner, R. G., et al., "Isolation and Purification of Protein Granules from *E. coli* Cells Overproducing bSt", Bio/Tech., 3:151–154 (1985).

The present invention discloses the use of detergents for placing somatotropins into a conformation that readily permits proper disulphide bond formation to take place in the presence of the detergent. Upon removal of the detergent the biologically active state is obtained. This is a nonobvious improvement over the Genentech patents which describe detergents as strong denaturants (0.01–2.0%). There the detergents are used to unfold proteins. The detergents are then removed before establishing disulphide bonds and folding the protein into the biologically active state.

In addition, none of the prior art known to the applicants describes a procedure having the advantages, efficiency and economic savings of the process herein disclosed.

SUMMARY OF THE INVENTION

This invention relates to general processes for extracting insoluble proteins from transformed microorganisms.

The invention specifically relates to an improved procedure to kill microorganisms prior to the extraction of protein. The cells are exposed to lethal amounts of toluene or xylene or combinations thereof. The use of nonpolar organic solvents is advantageous because such solvents are incapable of substantial protein disruption and denaturation. Unlike phenol, less polar organic solvents such as xylene or toluene will effectively kill microorganisms without a gross precipitation of host contaminants. Where the host cell expresses a substantial proportion of a desired natural or heterologous protein in a precipitated form, the avoidance of phenol is advantageous in that costs are reduced and higher yields obtained. Once killed the cells are lysed and standard procedures for protein extraction and purification are taken to obtain the desired protein.

The invention also discloses an advantageous oxidation step downstream from the killing step disclosed above. This step is particularly useful for recombinantly produced somatotropins which are insoluble within the cytoplasm of a transformed microorganism. Specifically, this step demonstrates that once the majority of host cell protein and contaminants are removed by the selective solubilization, using weakly denaturing detergents, the remaining insoluble somatotropins can be oxidized to the biologically active state using dissolved oxygen in a stronger solution of detergent. This is a single step conversion to the native disulphide bond orientation. The reshuffling and refolding steps described in the prior art are eliminated. The total removal of detergent is unnecessary and biological activity of the solution can be detected after dilution and injection into laboratory animals. Detergents useful for oxidations include sodium dodecyl sulfate (SDS) and those having a structure represented by formula I wherein n is 8–20, $R_1$ is methyl or ethyl and $R_2$ is hydrogen, methyl, ethyl, n-propyl or isopropyl. The preferred somatotropin for this step is rbSt.

An advantage of this improvement are the elimination of high molar salt solutions such as urea or guanidine. Such salts are difficult to handle under large scale commercial settings and are expensive. In addition, the use of detergents that are easily removed from the growth hormone allows for increased purity and permits renaturation and oxidation to occur at concentrations above 5 mg/ml where previous procedures teach that such concentrations will cause yield-reducing polymerization. U.S. Pat. No. 4,518,526. Finally, oxidation at higher concentrations will result in lower production cost due to lower process volumes.

In the above processes, the organism of choice is *E. coli*. The preferred killing solvent is toluene. The preferred detergent are those having a structure represented by formula 1 wherein the substituents and variables are as defined above. The most preferred detergent in which to oxidize rbSt to the native state is N-Lauroyl methylglycine.

In the above discussion and throughout this document the terms below have the following meanings.

"Biologically-active somatotropins from transformed microorganisms" refers to somatotropin that has been sufficiently restored to its native configuration that it has detectable activity In mammalian growth rate tests.

"Bovine somatotropin analogs" refer to proteins that are substantially similar to the longest forms of naturally occurring bSt and that have biological activity useful for increasing milk production and growth rates. Such analogs include both recombinantly produced rbSt having the same amino acid sequence as the heterogeneous species found in purified bSt from pituitary glands and those rbSt species artificially created by modifying bSt encoding DNA such as described in European patent application 103,395.

"Chaotropic agents" refer to protein denaturants which in aqueous solutions at suitable concentrations are capable of changing the spatial configuration or conformation of proteins through alterations at the surface thereof, either through altering the state of hydration, the solvent environment or solvent surface interaction. Examples of such agents include urea, guanidine, hydrochloride, sodium thiocyanate and detergents such as SDS and Triton X-100.

"Microorganisms" refer to both single cellular prokaryote and eukaryote organisms such as bacteria, yeast, actinomycetes and single cells from higher order plants or animals when being grown in cell culture as individual organisms.

"Oxidation" refers to a process in which the reduced thiol groups on cysteine residues of the proteins are crosslinked into the tertiary structure.

"Insoluble proteins" refers to any protein which does not dissolve in a particular aqueous environment such as in the cytoplasm of the microorganisms producing the protein or the initial homogenization medium. Functionally defined these proteins are those proteins that can be pelleted by standard ultracentrifugation procedures. The host cells are lysed in a suspension medium capable of maintaining the desired proteins insoluble from which they are separated from soluble materials by centrifugation. The general methods of isolation of insoluble proteins are known in art. See for example U.S. Pat. No. 4,512,922. Examples of insoluble proteins formed in microorganisms include, insulin, chymosin, somatotropins, crystal protein of Bucillus thuringlensis, fibroblast interferon, viral proteins, and tissue plasminogen activator.

"Insoluble forms of somatotropin" refers to precipitated forms of heterologous growth hormones being produced by a transformed organism. It is a type of insoluble protein.

"Selective solubilization" refers to a step in the extraction and purification procedure in which the host debris is solubilized and the desired insoluble protein remains insoluble.

"Somatotropin" refers to mammalian, fish and avian growth hormones. Somatotropins include analogs of these proteins wherein there is sufficient amino acid sequence identity to permit biologic activity to be maintained. Such analogs include recombinantly produced somatotropins having the same amino acid sequences as the heterogeneous species found in purified preparations from pituitary glands and analogs artificially created by modification of somatotropin encoding DNA such as described in European patent application 103,395.

"Transformed microorganism" refers to prokaryote or eukaryote single celled organism containing or hosting a plasmid artificially inserted into the cell using techniques well known in molecular genetics.

"Unbuffered alkaline solutions" refer to aqueous solutions having a pH above 7.0 and containing nonbuffering salts such as potassium or sodium hydroxide. Chelating agents such as ethylenediaminetetraacetic acid [EDTA] are optionally included. However, salts having significant buffering capacity are not added to these solutions. These solutions are used to suspend cells prior to lysis and retrieval of desired insoluble protein fractions.

DETAILED DESCRIPTION

The disclosed multistep procedure is optimally useful where the desired proteins are insoluble. Although the process was developed to isolate and purify insoluble heterologous proteins, the kill step of the process has general application to all insoluble proteins.

It is sometimes helpful to determine the proportion of desired protein that is in an insoluble form. In the case of heterologous proteins produced in transformed microorganisms strain variation may affect the proportion of insoluble to soluble protein. To determine the ratio of soluble to insoluble somatotropin as well as a comparison of yield between strains, radioimmunoassay is best. Cells producing somatotropins are lysed and labeled antibodies to the somatotropin which are added. The mixture is centrifuged and a comparison of the amount of label in the supernatant versus the pellet gives the ratio insoluble to soluble somatotropin being produced by the organism. U.S. Pat. No. 4,512,922, columns 25–26.

The various steps for isolation of somatotropins from transformed microorganisms are an effective cell kill, cell disruption, selective solubilizing or removal of undesired cellular debris, solubilizing of the somatotropin followed by further purification by filtration or dialysis and combinations thereof. Each step can be achieved in any number of ways known in the art.

Use of cell kill means are optional prior to cell disruption and several means are known in the art. Cell kill is useful from a safety perspective. In this invention cell kill is accomplished with a non-polar organic solvent which will minimize protein precipitation. The preferred solvents are toluene or xylene. The amount of solvent is dependent upon the concentration and type of cell being killed. It is determined empirically using standard viability tests. Ordinarily a lethal dose is defined as that concentration of solvent necessary to reduce the number of viable cells in a 10 ml sample to less than one. Viability is readily determined by culture techniques which vary according to the organism being exposed to the solvents. These techniques are known to those of ordinary skill in the art. Generally, it is necessary to add amounts of solvent beyond the saturation point of the aqueous layer. Amounts in excess of the minimum lethal dose are not harmful to the process although containment of inflammable fumes must be taken into account to ensure adequate safety.

After killing the microorganisms, the cells are disrupted by any number of known means, such as by sonication, pressure, or detergent. The preferred method-will not heat the solution and yield high levels of cellular rupture. The preferred method is to use a homogenizer such as a Manton-Gaulin to disrupt the cells. A second cycle of disruption is also helpful.

The disrupted cells are suspended in a buffer of low ionic concentration under alkaline conditions or in deionized water at a pH of 8–10.5. The solution is kept between 2°–15° C. and immediately treated with detergents that selectively solubilized cell membranes and other undesired cellular debris while not solubilizing the somatotropins. Effective detergents for rbSt include: Triton X-100 and deoxycholate, with Tergitol 15-5-7 being preferred. Sodium borate is the preferred buffer.

The solubilized cell debris is mechanically separated from insoluble somatotropin by centrifugation sufficient to sediment the solids. The sediments are then repeatedly suspended in the above buffer and recentrifuged to eliminate the solubilized cellular debris.

The Insoluble somatotropins are next solubilized and oxidized under controlled conditions. The conditions are designed to minimize undesirable polymerization which would reduce yields.

Using SDS or a detergent of formula I wherein n is 8 through 20 inclusive; $R_1$ is methyl or ethyl; and $R_2$ is hydrogen, ethyl, methyl or n-propyl, solubilization and oxidation of somatotropins can be achieved at relatively high concentrations. The ratio of somatotropin to detergent is dependent on the detergent's acid moiety: the weaker the acid moiety of the detergent, the greater quantity of detergent required for solubilization. For example, using sodium dodecyl sulfate which has a relatively strong acid moiety, a ration of 1:1 is sufficient. However, using detergents of formula I, ratios of 2–5 are preferred. Use of a buffer to dilute the detergent is optional.

Once the somatotropin is solubilized, the oxidation is optionally promoted by introducing air through the mixture. Air is introduced by either agitation or passing air directly through the solution. The rate and method of introduction of air is dependent on the quantity of the preparation. It is necessary to allow oxidation to go to completion to avoid downstream polymerization reagent during concentration. Oxidation can be monitored by use of Ellman's reagent. Methods of Enzymology, 25:457–464 (1972).

The preferred method for solubilizing rbSt is to add an aqueous solution of N-Lauroyl methylglycine (Hamposyl R L-95, W. R. Grace, Lexington, Mass.) in a sodium borate buffer at 0.1–0.5 M and pH 8–10.5. The amount of Hamposyl needed to solubilize rbSt is approximately 2–10 g for each gram of rbSt present with a 4:1 ratio being preferred. Less detergent reduces the solubility of rbSt and more detergent will increase production costs. The solution is then agitated at 15–25° C. while air is passed through the mixture for at least 16 hours.

The detergent is then removed by anion exchange resin. The preferred ion exchange resin is Dowex 1×4 in the chloride form (Dow Chemical Co.). The resin is removed by filtration and fresh resin added and removed until the mixture is essentially detergent free. Upon removal of detergent, the rbSt is split into two populations, monomers and large polymeric bodies. The polymeric material forms a precipitate which is readily removable as described in the next step. The remaining somatotropin is in the monomeric and native form.

The detergent-free mixture is further purified by removal of remaining solid contaminants including polymeric rbSt. Said contaminants are removed by techniques well-known in the art, such as centrifugation or microfiltration. The preferred method is to use filter aids such, as CELATOM (Eagle-Picher, Cincinnati, Ohio) or SUPERCEL (The Johns-Manville Co., New York, N.Y.) which are added and removed by filtration. The filtrate may be passed through a microfilter having pore sizes of 0.45 microns.

The filtrate is concentrated by ultrafiltration. The preferred filtration membrane being 10,000 molecular weight cut-off polysulfone membranes. The somatotropin which has a molecular weight of over approximately 20,000 is retained and the retentate is dialyzed against water, pH 9–10 with base such as ammonium or sodium hydroxide. Because rbSt is apt to form colloids at high concentrations which deposit on the filter, it is helpful to pass alkaline water through the filtering device to avoid substantial losses at this point.

The somatotropin can be dialyzed and freeze dried at this point or further purified by passage through an ion exchange column, such as DEAE sepharose. The column is kept under alkaline conditions of 9.0–10.5. Fractions containing somatotropin are collected from the column.

The fractions are concentrated using ultrafiltration or other similar methods and the concentrate filtered a final time through a microfilter. The polished permeate is then freeze dried.

Without further elaboration, it is believed that one skilled in the art can, using the preceding description, practice the present invention to its fullest extent. The following detailed example describes how to perform the processes of the invention and is to be construed as merely illustrative, and not limitations of the preceding disclosure in any way whatsoever. Those skilled in the art will promptly recognize appropriate variations from the procedures as to reactants, conditions and techniques.

EXAMPLES

Example 1

Extraction of bSt from *E. coli* and Oxidation to the Native State.

Step 1. Killing *E. coli* with Toluene.

Transformed *E. coli* expressing bSt can be obtained from the American Type Culture Collection (ATCC No. 31826) or from other commonly known sources. The cells are grown in a fermenter and harvested under conditions appropriate to turn on the particular promotor present, such as described in European Patent Application 131 893 A1 for *E. coli* ATCC 31826 or U.S. Pat. No. 4,511,503.

Ten kg of wet cells having a dry weight of 3.5 grams of cells and containing 50 mg rbSt/gm wet cells are placed into a container in which the oxygen is reduced to less than 5% through the introduction of nitrogen while agitating the solution. This is a cell slurry of 200 liters. To this slurry is added 6.7 liters of toluene and the slurry is agitated. for 1 hour at 15° C.

Step 2. Rupture of the Cells.

The dead cells are centrifuged with a Westfalia solids discharging centrifuge at 12,000×g at 4 lpm. The cell pellet is resuspended in deionized water to a total volume of 46 liters. Thirty-five grams of EDTA is added and the pH adjusted to 9.0 with 1N NaOH. The cells are agitated until a uniform suspension is formed and cooled to 5° C. prior to homogenization in a Gaulin homogenizer. The Gaulin homogenizer is operated at 9,000 psig. The ruptured cells are cooled to 5° C. as soon as possible and homogenized a second time at 10,000 psig. The product is then cooled to 20° C. as soon as possible.

Step 3. Detergent and Buffer Washes.

To the suspension is added 2 liters of Tergitol 15-5-7. The solution is agitated for 30 minutes and centrifuged in the Westfalia solids discharging centrifuge (12000 g) at 2 lpm. The resulting pellet is suspended in 50 liters of deionized water and agitated for 15 minutes until uniformly suspended. The suspension is adjusted to a pH of 8–9 with iN NaOH and recentrifuged in the Westfalia solids discharging centrifuge (12000 g) at 2 lpm.

Step 4. Solubilization of bSt and Oxidation.

The solid is immediately suspended in 50 liters of 100 mM sodium borate buffer at pH 10.0 containing 1.5 kg of N-lauroyl methylglycine (Hamposyl L-95). The solution is vigorously agitated for 1 hr at 20° C. to completely solubilize the pellet and then gently agitated at 20° C. while adding air at 5 cubic feet per hr for at least 16 hours.

Step 5. Removal of Hamposyl with Dowex 1×4.

The pH of the Hamposyl extract is adjusted to 10.5 with 1N NaOH. The extract is then fed at a rate of 400 ml/minute to a 75 liter column of Dowex 1×4 in chloride form. The column is washed with 45 liters of 50 mm sodium borate at pH 10.0 and the fractions containing rbSt are collected.

Step 6. Polishing of the Hamposyl—Free Extract.

Three kg of standard Supercel are added to the above solution and the solution is then agitated to obtain a uniform suspension. The mixture is then filtered on a filter press. The resulting filter cake is washed with 12 liters of 50 mM sodium borate at pH 10.0. The wash and the filtrate are then combined.

Step 7. Ultrafiltration.

Using a 10,000 molecular weight cut off polysulfone membrane, the combined filtrate and wash solutions from Step 6 are concentrated to 4 liters. The concentrated solution is then diafiltered while maintaining a retentate volume constant using 40 liters of pyrogen-free water which was pH adjusted to 10.3 with 1N NaOH. The retentate is collected and the ultrafilter washed with 6 liters of deionized water pH adjusted to 10.3.

Step 8. DEAE Sepharose Ion Exchange.

The rbSt concentrate is then fed through a column of DEAE sepharose in carbonate form. The sepharose is equilibrated with 5 mM sodium carbonate at pH 9.2. The concentrate is fed to the sepharose column at a rate of 30 ml/minute and it is followed by 6 liters of 5 mM sodium carbonate buffer at a pH of 9.2 at a rate of 300 ml/minute. The column is then eluted using 300 liters of 150 mM sodium carbonate buffer at pH 9.2, being fed to the column at a rate of 300 ml/minute. Fractions containing rbSt are saved.

Step 9. Ultrafiltration of the Eluate.

The fractions containing rbSt are adjusted to a pH of 10.0 using 1N NaOH and concentrated using a 10,000 molecular weight cut-off polysulphone membrane to 4 liters. The 4 liters of solution are then diafiltered while maintaining a retentate volume constant using 40 liters of pyrogen-free water that has been pH adjusted to 10.3 with NaOH. The retentate is collected and the ultrafilter washed with 3 liters of deionized water pH adjusted to 10.3. The retentate and wash solutions are then combined.

Step 10. Final Polish and Freeze Drying.

The retentate and wash solutions from Step 10 are concentrated to 400 ml using a Pellicon R (Millipore Corp., Bedford, Mass.) filter containing 5 square feet of a 0.45μ Durapore membrane. The concentrate is then diafiltered while maintaining a constant retentate volume using 2.4 liters of pyrogen-free water pH adjusted to 10.3 with NaOH. The permeate is then freeze dried.

FORMULA I

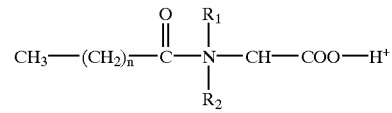

What is claimed is:

1. A process for purifying an insoluble protein from a microorganism comprising:
   1) killing the microorganism by exposure to a lethal amount of an organic solvent consisting essentially of toluene;
   2) lysing the microorganism; and
   3) recovering the insoluble protein.

2. The process according to claim 1 wherein the insoluble protein is bovine somatotropin or a bovine somatotropin analog.

3. The process according to claim 2 wherein the microorganism is *Escherichia coli*.

4. The process according to claim 1 wherein the microorganism is *Escherichia coli*.

5. A process for purifying an insoluble protein from a microorganism comprising:
   1) killing the microorganism by exposure to a lethal amount of an organic solvent consisting essentially of toluene and xylene;
   2) lysing the microorganism; and
   3) recovering the insoluble protein.

6. The process according to claim 5 wherein the insoluble protein is bovine somatotropin or a bovine somatotropin analog.

7. The process according to claim 6 wherein the microorganism is *Escherichia coli*.

8. The process according to claim 5 wherein the microorganism is *Escherichia coli*.

9. A process for purifying an insoluble protein from a microorganism comprising:
   1) killing the microorganism by exposure to a lethal amount of xylene;
   2) lysing the microorganism; and
   3) recovering the insoluble protein.

10. The process according to claim 9 wherein the insoluble protein is bovine somatotropin or a bovine somatotropin analog.

11. The process according to claim 10 wherein the microorganism is *Escherichia coli*.

12. The process according to claim 9 wherein the microorganism is *Escherichia coli*.

* * * * *